(12) United States Patent
Takaoka et al.

(10) Patent No.: US 9,393,065 B2
(45) Date of Patent: Jul. 19, 2016

(54) STIRRING METHOD AND ABLATION CATHETER SYSTEM WITH BALLOON

(75) Inventors: Motoki Takaoka, Otsu (JP); Akinori Matsukuma, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 855 days.

(21) Appl. No.: 13/260,793

(22) PCT Filed: Mar. 30, 2010

(86) PCT No.: PCT/JP2010/055631
§ 371 (c)(1),
(2), (4) Date: Sep. 28, 2011

(87) PCT Pub. No.: WO2010/113913
PCT Pub. Date: Oct. 7, 2010

(65) Prior Publication Data
US 2012/0035604 A1 Feb. 9, 2012

(30) Foreign Application Priority Data

Mar. 31, 2009 (JP) .................................. 2009-085006

(51) Int. Cl.
*A61B 18/04* (2006.01)
*A61B 18/00* (2006.01)

(52) U.S. Cl.
CPC ....... *A61B 18/04* (2013.01); *A61B 2018/00577* (2013.01); *A61B 2018/046* (2013.01)

(58) Field of Classification Search
CPC ............. A61B 18/04; A61B 2018/044; A61B 2018/046; A61B 2018/1465
USPC .......................... 606/27–31, 41; 607/101–102
See application file for complete search history.

(56) References Cited

U.S. PATENT DOCUMENTS

| | | | | |
|---|---|---|---|---|
| 5,168,880 | A * | 12/1992 | Sogawa et al. | 607/102 |
| 8,647,339 | B2 * | 2/2014 | Satake | 606/33 |
| 2003/0065371 | A1 | 4/2003 | Satake | |
| 2007/0149964 | A1 | 6/2007 | Kawabata et al. | |
| 2008/0039790 | A1* | 2/2008 | Hasebe | 604/113 |

FOREIGN PATENT DOCUMENTS

| | | |
|---|---|---|
| EP | 1433448 A1 | 6/2004 |
| EP | 1442719 A1 | 8/2004 |

(Continued)

OTHER PUBLICATIONS

International Application Serial No. PCT/JP2010/055631, International Search Report mailed May 11, 2010, 2 pgs.

*Primary Examiner* — George Evanisko
(74) *Attorney, Agent, or Firm* — RatnerPrestia

(57) ABSTRACT

Provided is an ablation catheter system with a balloon which can improve the effect of therapy by ablation by eliminating variation in the surface temperature of a balloon in the ablation catheter with a balloon which cauterizes the tissue. An ablation catheter system with a balloon comprising a catheter shaft, a balloon fixed to the catheter shaft, a lumen which penetrates the catheter shaft in the direction of the long axis and communicates with the interior of the balloon, a heating electrode arranged in the balloon, a heating device which applies electrical energy to the heating electrode, and a vibration imparting device which imparts a vibration to the heating liquid by periodically repeating suction and ejection of the heating liquid from the lumen. Also provided is a stirring method for stirring the heating liquid by vibration wherein the vibration is imparted in such a manner that the value obtained by dividing the volume of the heating liquid being ejected toward the balloon by single ejection by the expansion volume of the balloon and then multiplying the quotient by 100 becomes 2-9.

3 Claims, 6 Drawing Sheets

(56) References Cited

FOREIGN PATENT DOCUMENTS

| | | | |
|---|---|---|---|
| EP | 1946712 | A1 | 7/2008 |
| JP | 3607231 | B2 | 1/2005 |
| JP | 3892438 | B2 | 3/2007 |
| JP | 4151910 | B2 | 9/2008 |

\* cited by examiner

STIRRING METHOD AND ABLATION CATHETER SYSTEM WITH BALLOON

CROSS-REFERENCE TO RELATED APPLICATIONS

This application is the U.S. National Phase application of PCT International Application No. PCT/JP2010/055631, filed Mar. 30, 2010, and claims priority to Japanese Patent Application No. 2009-085006, filed Mar. 31, 2009, the disclosures of which PCT and priority applications are incorporated herein by reference in their entirely for all purposes.

TECHNICAL FIELD

The present invention relates to a mixing method and an ablation catheter system with a balloon.

BACKGROUND OF THE INVENTION

Catheter ablation is an arrhythmia treatment method of inserting an ablation catheter into a cardiac chamber and applying heat between a tip electrode and a counter electrode plate to ablate a myocardial tissue. The catheter ablation is conducted mainly for treatment of tachyarrhythmia such as a paroxysmal supraventricular tachycardia, an atrial tachycardia, an atrial flutter, and a paroxysmal ventricular tachycardia and is a technique of diagnosing a pathogenetic mechanism and a genesis region of an arrhythmia in a cardiac electrophysiological test, thereafter making an electrode of an ablation catheter reach the genesis region of the arrhythmia from the interior of a cardiac chamber, and repeating an operation of applying the electrode to a causative myocardial tissue in the region and heating the tissue at 53 to 60° C. for approximately 60 seconds.

Since many of the ablation catheters currently in use have a metallic electrode having a length of 4 to 8 mm and a diameter of 2 to 3 mm at a tip portion of a catheter shaft, each of such catheters generally adopts a technique of bringing the metallic electrode into contact with a myocardial tissue that causes an arrhythmia in a dotted manner and forming an ablation line while moving the electrode little by little to isolate the source of the arrhythmia (Patent Literature 1).

However, the ablation catheter having the metallic electrode requires several dozen times of repeated ablations to form the ablation line and isolate the source of the arrhythmia and thus causes problems of a prolonged operation and a heavy burden imposed on a patient. Also, since the small metallic electrode needs to be brought into contact with the target region of the myocardial tissue accurately to form the ablation line with the ablation catheter, a physician requires an advanced technique to manipulate the ablation catheter. Further, since the myocardial tissue is ablated in the dotted manner, an insufficient ablation line with spaces between the ablated parts may be formed, in which case the source of the arrhythmia cannot be isolated completely, which may cause recurrence of the arrhythmia.

Recently, an ablation catheter with a balloon having a balloon at the tip of a catheter shaft has been developed, and an ablation catheter system with a balloon including a radio-frequency generating device and a balloon surface temperature uniforming device has been reported (Patent Literatures 2 and 3).

The ablation catheter system with a balloon is a system of expanding a balloon fixed to the tip of a catheter by a liquid for heating and heating the liquid for heating by a radio-frequency current supplied from a radio-frequency generating device to ablate the entire myocardial tissue contacting the surface of the balloon. The temperature of the balloon surface is adjusted by a balloon surface temperature uniforming device such as a vibration imparting device, which imparts a vibration to the liquid for heating filled in the balloon, and is controlled by a temperature sensor arranged in the balloon.

PATENT LITERATURE

Patent Literature 1: Japanese Patent No. 4151910
Patent Literature 2: Japanese Patent No. 3607231
Patent Literature 3: Japanese Patent No. 3892438

SUMMARY OF THE INVENTION

In the treatment with use of the ablation catheter system with a balloon, the balloon size needs to be adjusted arbitrarily in accordance with histological characteristics of a patient and a state of the trigger region of the arrhythmia, in which case it is difficult to keep the balloon surface temperature uniform in accordance with a size variation of the balloon by the vibration imparting device as a balloon surface temperature uniforming means disclosed in Patent Literatures 2 and 3.

Also, taking time up to keeping the balloon surface temperature uniform leads to a prolonged operation after insertion of the catheter, which causes a problem of a heavy burden imposed on the patient.

The present invention can eliminate a variation in a surface temperature of a balloon in an ablation catheter with a balloon, uniform the balloon surface temperature in a short time, and improve an effect of treatment by an ablation catheter system with a balloon.

As a result of concerted study directed toward solving the aforementioned problem, the present inventors arrived at the present invention upon discovering that, in order to eliminate a variation in a surface temperature of a balloon in an ablation catheter with a balloon, not repeating suction and ejection of a large amount of liquid for heating intensively but repeating suction and ejection of a small amount of liquid for heating within a predetermined range is effective at the time of imparting a vibration to the liquid for heating in the balloon by periodically repeating suction and ejection of the liquid for heating.

That is, the present invention provides a stirring method for stirring a liquid for heating by a vibration in an ablation catheter system with a balloon including a catheter shaft, a balloon fixed to the catheter shaft, a lumen passing through the catheter shaft in a direction of a long axis to communicate with an interior of the balloon, a heating electrode arranged in the interior of the balloon, a heating device applying an electric energy to the heating electrode, and a vibration imparting device imparting the vibration to the liquid for heating by periodically repeating suction and ejection of the liquid for heating from the lumen, wherein the vibration is imparted to the liquid for heating so that a value derived by dividing a volume of the liquid for heating to be ejected from the lumen toward the balloon at a single time by an expansion volume of the balloon and multiplying the quotient by 100 becomes 2 to 9.

The vibration imparting device is preferably a device that repeats the suction and the ejection of the liquid for heating 1 to 5 times per second.

The present invention also provides an ablation catheter system with a balloon including a catheter shaft, a balloon fixed to the catheter shaft, a lumen passing through the catheter shaft in a direction of a long axis to communicate with an interior of the balloon, a heating electrode arranged in the interior of the balloon, a heating device applying an electric energy to the heating electrode, and a vibration imparting device imparting a vibration to the liquid for heating by periodically repeating suction and ejection of the liquid for heating from the lumen, wherein the vibration is imparted to the liquid for heating so that a value derived by dividing a volume of the liquid for heating to be ejected from the lumen toward the balloon at a single time by an expansion volume of the balloon and multiplying the quotient by 100 becomes 2 to 9.

The vibration imparting device is preferably a device that repeats the suction and the ejection of the liquid for heating 1 to 5 times per second and preferably has a pump selected from a group consisting of a roller pump, a diaphragm pump, a bellows pump, a vane pump, a centrifugal pump, and a pump constituted by combination of a piston and a cylinder.

With the present invention, it is possible to keep a surface temperature of a balloon of various sizes provided in an ablation catheter with a balloon uniform and to shorten the amount of time required to keep the balloon surface temperature uniform. Also, with the present invention, since unevenness of ablated regions can be eliminated, an effect of treatment can be improved, and a burden on a patient can be drastically reduced.

BRIEF DESCRIPTION OF THE DRAWINGS

FIGS. 2(A) and 2(B) are schematic cross-sectional views along the line A-A' of a catheter shaft used in the ablation catheter system with a balloon in FIG. 1, wherein FIG. 2(A) is an example of the catheter shaft having one lumen, and FIG. 2(B) is an example of the catheter shaft having two lumens.

Figure 1:
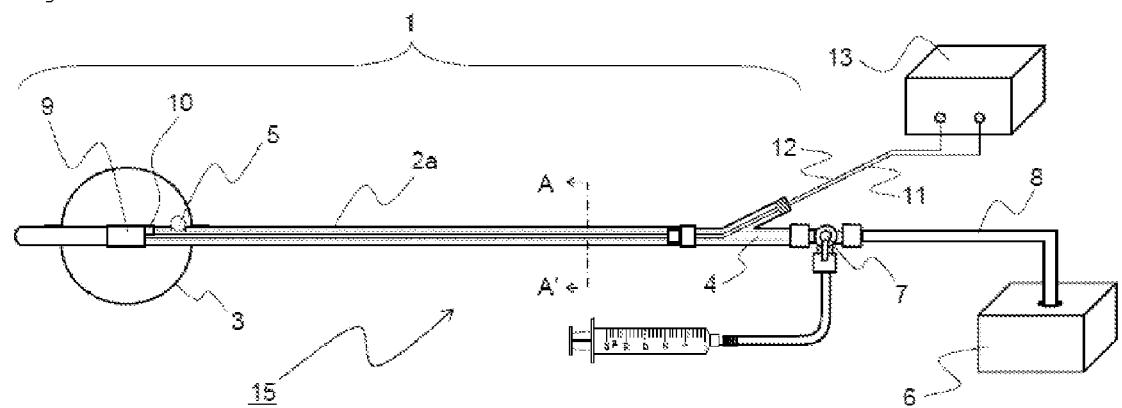
FIG. 1 is a schematic view of an exemplary embodiment of an ablation catheter system with a balloon.

DESCRIPTION OF PREFERRED
EMBODIMENTS OF THE INVENTION

Preferred embodiments of the present invention will be described below with reference to the accompanying drawings, but the present invention is not limited to these embodiments. Like reference characters designate similar or identical parts throughout the several views thereof, and duplicate explanation is omitted. Also, the ratio in the drawings does not necessarily correspond to an actual ratio.

A stirring method according to an embodiment of the present invention is a stirring method for stirring a liquid for heating by a vibration in an ablation catheter system with a balloon including a catheter shaft, a balloon fixed to the catheter shaft, a lumen passing through the catheter shaft in a direction of a long axis to communicate with an interior of the balloon, a heating electrode arranged in the interior of the balloon, a heating device applying an electric energy to the heating electrode, and a vibration imparting device imparting the vibration to the liquid for heating by periodically repeating suction and ejection of the liquid for heating from the lumen, wherein the vibration is imparted to the liquid for heating so that a value derived by dividing a volume of the liquid for heating to be ejected from the lumen toward the balloon at a single time by an inflation volume of the balloon and multiplying the quotient by 100 becomes 2 to 9.

FIG. 1 is a schematic view of an ablation catheter system with a balloon according to an exemplary embodiment of the present invention.

An ablation catheter system with a balloon 15 shown in FIG. 1 is roughly constituted by an ablation catheter with a balloon 1, a vibration imparting device 6, and a heating device 13.

The ablation catheter with a balloon 1 has on a front side of a catheter shaft 2a a balloon 3 that can inflate and deflate, and a front portion and a rear portion of the balloon 3 are fixed to the catheter shaft 2a. The catheter shaft 2a has a lumen 4 passing through its interior, and the lumen 4 communicates with an interior of the balloon 3 by a side hole 5 at a front portion of the catheter shaft 2a. The lumen 4 on a proximal side of the catheter shaft 2a is connected to the vibration imparting device 6 via a three-way stopcock 7 and a pressure-resistant extension tube 8. A heating electrode 9 is fixed to the catheter shaft 2a in the interior of the balloon 3, and a temperature sensor 10 is fixed to a proximal end of the heating electrode 9. A heating electrode lead wire 11 connected to the heating electrode 9 and a temperature sensor lead wire 12 connected to the temperature sensor 10 are connected to the heating device 13 through the lumen 4.

The length of the catheter shaft 2a is preferably 0.5 to 2 m from a viewpoint of making the balloon 3 reach a myocardial tissue.

The diameter of the catheter shaft 2a is preferably 3 to 5 mm from a viewpoint of inserting it into a blood vessel.

A material for the catheter shaft 2a is preferably a flexible material with excellent antithrombogenicity such as a fluorine resin, a polyamide resin, a polyurethane resin, or a polyimide resin.

From a viewpoint of enabling the balloon 3 to closely contact a genesis region of an arrhythmia, the diameter of the balloon 3 is preferably 20 to 40 mm, the shape is preferably a spherical shape, and the film thickness is preferably 20 to 100 µm.

A material for the balloon 3 is preferably a stretchable material with excellent antithrombogenicity and is more preferably a polyurethane polymeric material.

Examples of the polyurethane polymeric material include thermoplastic polyether urethane, polyether polyurethane urea, fluorine polyether urethane urea, a polyether polyurethane urea resin, and polyether polyurethane urea amide.

Figure 2:
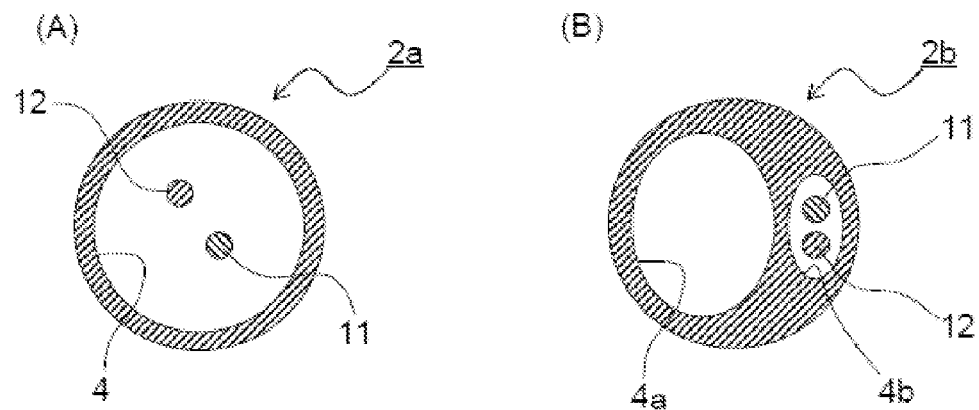

The cross-sectional area of the lumen 4 in a cross-section perpendicular to a longitudinal direction of the catheter shaft 2a is preferably 3 to 12 mm² from a viewpoint of enabling to supply a liquid for heating 14 smoothly from the three-way stopcock 7 with use of a syringe, and the inner diameter of the lumen 4 is preferably 2 to 4 mm when the lumen 4 is cylindrical as shown in FIG. 2(A).

The catheter shaft may be a double-lumen catheter shaft 2b having a lumen 4a that communicates with the interior of the balloon 3 and through which the liquid for heating 14 passes and a lumen 4b into which the heating electrode lead wire 11 and the temperature sensor lead wire 12 are inserted as shown in FIG. 2(B).

Figure 3:
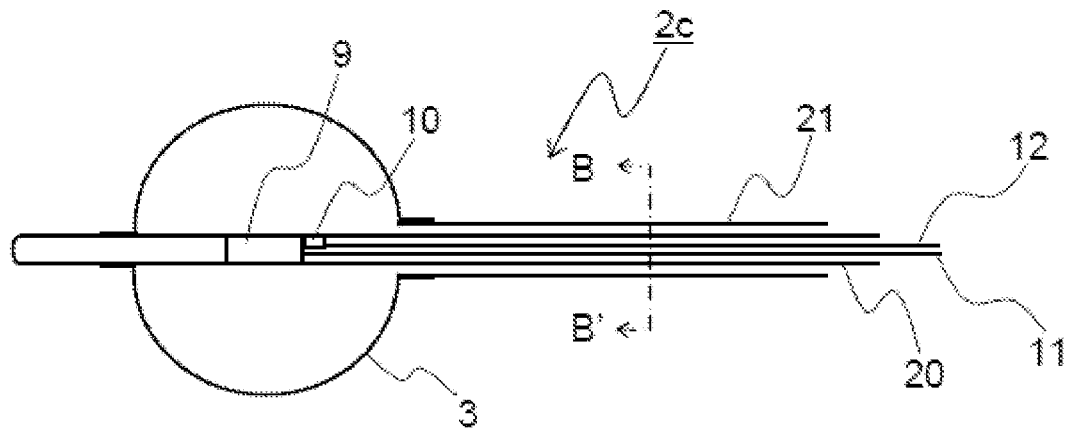
FIG. 3 is a schematic view showing a second example of an ablation catheter with a balloon that can be used in the ablation catheter system with a balloon in FIG. 1.
Figure 4:
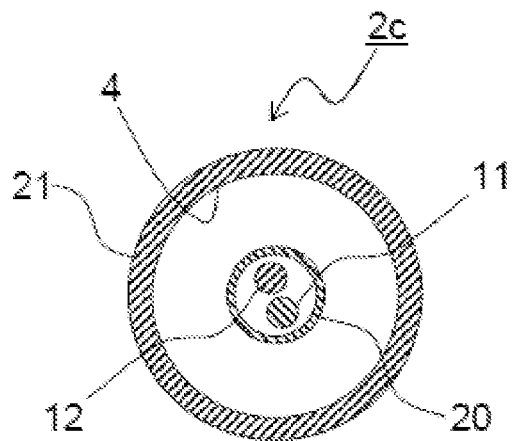
FIG. 4 is a schematic cross-sectional view along the line B-B' of the catheter shaft in FIG. 3.
Figure 5:
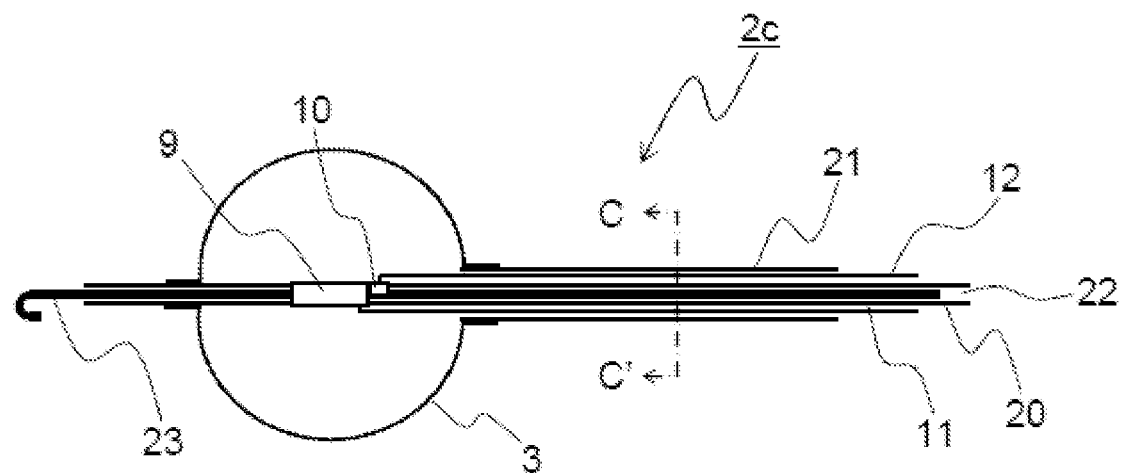
FIG. 5 is a schematic view showing a third example of the ablation catheter with a balloon that can be used in the ablation catheter system with a balloon in FIG. 1.
Figure 6:
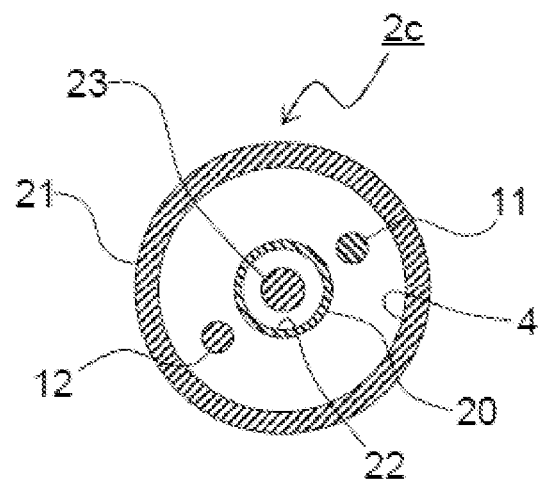
FIG. 6 is a schematic cross-sectional view along the line C-C' of the catheter shaft in FIG. 5.

Also, the catheter shaft may be a double-pipe catheter shaft 2c in which an inner pipe 20 is inserted into a lumen of an outer pipe 21 as shown in FIG. 3 or 5. In this case, a space between the outer pipe 21 and the inner pipe 20 preferably communicates with the interior of the balloon 3, and the heating electrode lead wire 11 and the temperature sensor lead wire 12 are preferably inserted into the inner pipe 20 as a lumen, as shown in FIG. 4 corresponding to FIG. 3. Alternatively, a space between the outer pipe 21 and the inner pipe 20 preferably communicates with the interior of the balloon 3, the heating electrode lead wire 11 and the temperature sensor lead wire 12 are preferably inserted into the space, and a guidewire 23 is preferably inserted into the inner pipe 20 as a lumen, as shown in FIG. 6 corresponding to FIG. 5.

In the case of the double-pipe catheter shaft 2c, the front portion of the balloon 3 is preferably fixed to a front portion of the inner pipe 20 in the longitudinal direction while the rear portion of the balloon 3 is preferably fixed to a front portion of the outer pipe 21 in the longitudinal direction, as shown in FIG. 3 or 5.

Preferably, the area of the side hole 5 is approximately as large as the cross-sectional area of the lumen 4 in the cross-section perpendicular to the longitudinal direction of the catheter shaft 2a.

As for a location to provide the side hole 5, the side hole 5 is preferably provided around the front portion of the balloon 3 or the rear portion of the balloon 3 from a viewpoint of generating eddy current in the interior of the balloon by suction and ejection of the liquid for heating 4, but a plurality of side holes may be provided in a spiral manner. Meanwhile, in the case of the double-pipe catheter shaft 2c shown in FIG. 3 or 5, no side hole 5 needs to be provided.

The heating electrode 9 is fixed to the catheter shaft 2a in the interior of the balloon 3. From a viewpoint of improving flexibility in a range in which the heating electrode 9 is fixed, the heating electrode 9 may be divided into plural pieces and fixed.

Examples of a method for fixing the heating electrode 9 to the catheter shaft 2a include caulking, adhesion, welding, and a heat shrinkable tube.

The shape of the heating electrode 9 is preferably a tubular shape such as a coiled shape or a cylindrical shape with a length of 10 to 20 mm.

The diameter of an electric wire of the coiled heating electrode 9 is preferably 0.1 to 1 mm from a viewpoint of practicality.

Examples of a material for the heating electrode 9 include gold, silver, platinum, copper, and an alloy of these metals.

The heating electrode lead wire 11 connected to the heating electrode 9 is inserted into the lumen 4 and is connected to the heating device 13.

The diameter of the heating electrode lead wire 11 is preferably 0.1 to 1 mm from a viewpoint of practicality.

Examples of a material for the heating electrode lead wire 11 include copper, silver, gold, platinum, tungsten, and an alloy of these metals, and the heating electrode lead wire 11 is preferably provided with an electrical insulating protective coat such as a fluorine resin from a viewpoint of preventing short circuit.

The heating device 13 is preferably a radio-frequency generating device, and the frequency of radio-frequency currents to be supplied to the heating electrode 9 is preferably 100 kHz or higher from a viewpoint of preventing an electric shock of a patient.

The temperature sensor 10 is preferably fixed to the heating electrode 9 or the catheter shaft 2a from a viewpoint of measuring a temperature of the interior of the balloon 3 in a stable manner but may be fixed to an inner surface of the balloon 3 from a viewpoint of measuring a surface temperature of the balloon 3.

Examples of the temperature sensor 10 include a thermocouple and a resistance-temperature detector.

The temperature sensor lead wire 12 connected to the temperature sensor 10 is inserted into the lumen 4 and is connected to a temperature control unit in the heating device 13.

The diameter of the temperature sensor lead wire 12 is preferably 0.05 to 0.5 mm from a viewpoint of practicality.

Examples of a material for the temperature sensor lead wire 12 include copper, silver, gold, platinum, tungsten, and an alloy of these metals when the temperature sensor 10 is a resistance-temperature detector, and the temperature sensor lead wire 12 is preferably provided with an electrical insulating protective coat such as a fluorine resin from a viewpoint of preventing short circuit. Also, when the temperature sensor 10 is a thermocouple, a material for the temperature sensor lead wire 12 is preferably the same material as that for the thermocouple, and examples of the material include copper and constantan when the temperature sensor 10 is a Type T thermocouple while examples of the material include chromel and alumel when the temperature sensor 10 is a Type K thermocouple.

The liquid for heating 14 is preferably a contrast medium or a contrast medium diluted with saline from a viewpoint of enabling the expanded balloon 3 to be confirmed on an X-ray fluoroscopic image. Meanwhile, in a case where the heating electrode 9 is to be supplied with radio-frequency currents, the liquid for heating 14 is preferably an ionic contrast medium or a contrast medium diluted with saline from a viewpoint of being conductive.

The vibration imparting device 6 is connected to the ablation catheter with a balloon 1 via the three-way stopcock 7 and the pressure-resistant extension tube 8.

Examples of the vibration imparting device 6 include a roller pump and a pump constituted by combination of a piston and a cylinder.

Figure 7:
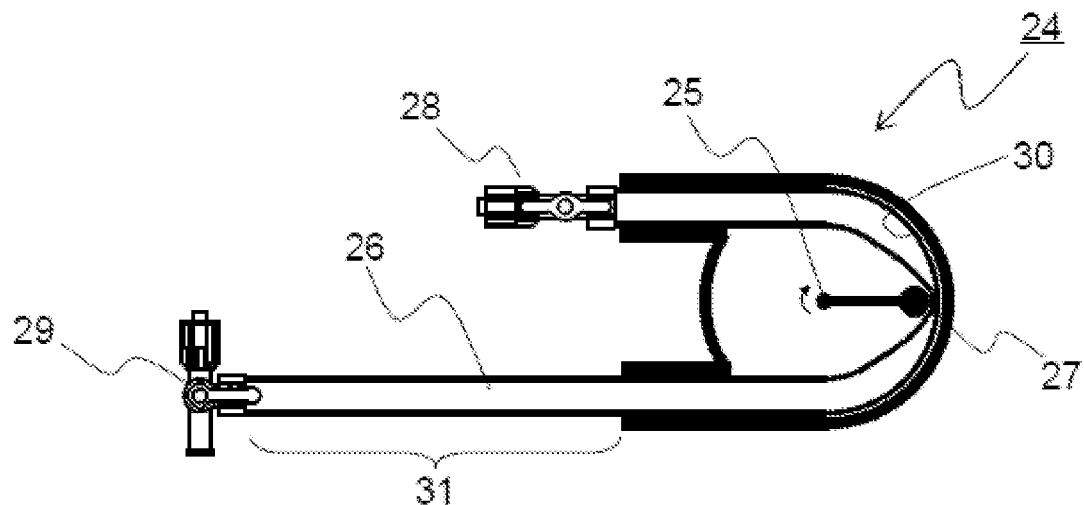
FIG. 7 is a schematic view showing a first example of a vibration imparting device in the ablation catheter system with a balloon in FIG. 1.
Figure 8:
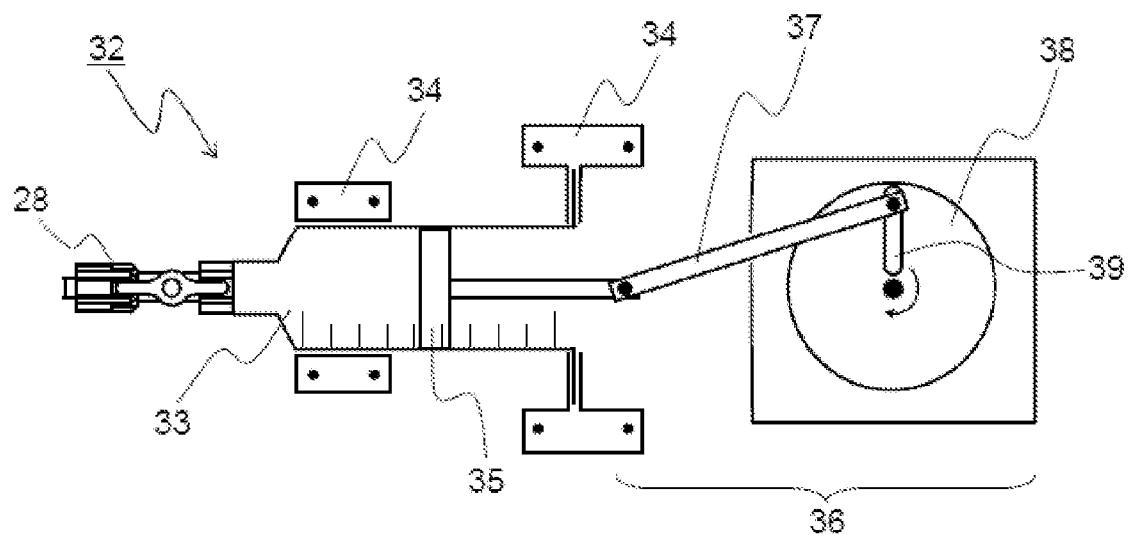
FIG. 8 is a schematic view showing a second example of the vibration imparting device in the ablation catheter system with a balloon in FIG. 1.

FIG. 7 is a schematic view showing a first example of the vibration imparting device in the ablation catheter system with a balloon in FIG. 1, that is, a vibration imparting device 24.

A roller 27 is rotated and driven by a motor around a rotating shaft 25. When the roller 27 is opposed to a guide surface 30, mutually opposing tube walls of an elastic tube 26 closely contact, the elastic tube 26 is closed, and a reservoir portion 31 is pressurized. On the other hand, when the roller 27 is not opposed to the guide surface 30, the elastic tube 26 is expanded to have an original diameter by an elastic restoring effect, the elastic tube 26 is in a communicating state, and the pressure of the reservoir portion 31 is released. In this manner, periodically repeating suction and ejection of the liquid from the reservoir portion 31 toward the balloon 3 by rotation of the roller 27 enables a vibration to be imparted to the liquid for heating.

A material for the elastic tube 26 is preferably silicone from a viewpoint of easy elastic restoration.

Figure 9:
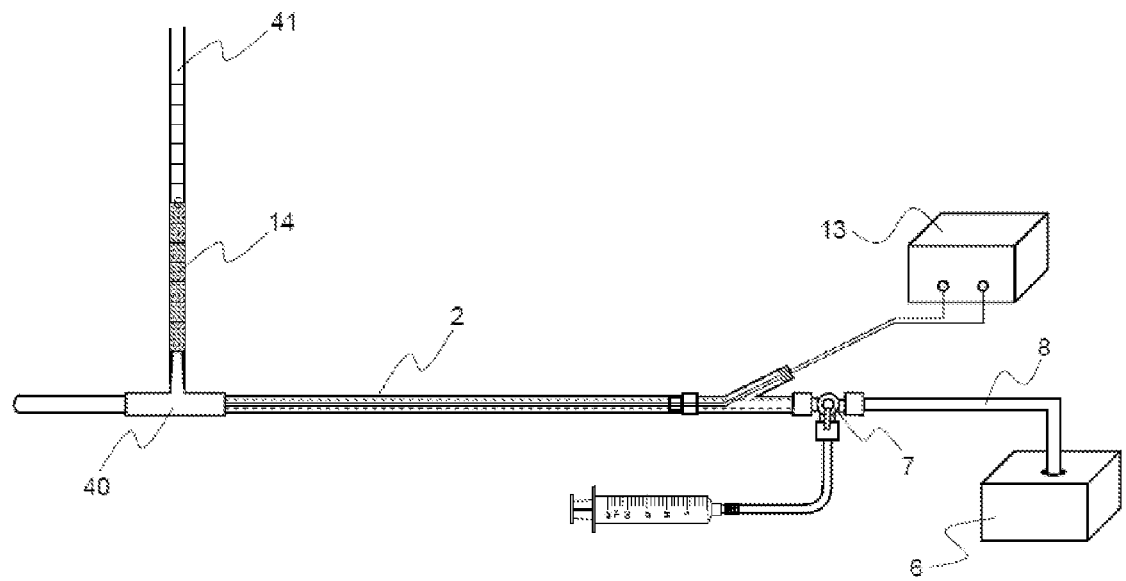
FIG. 9 shows an experimental system to measure a volume of a liquid for heating to be sucked or ejected from the lumen by the vibration imparting device.

FIG. 9 is a schematic view showing a second example of the vibration imparting device in the ablation catheter system with a balloon in FIG. 1, that is, a syringe-type vibration imparting device 32 that is a pump constituted by combination of a piston and a cylinder.

A rear end of a piston 35 inserted into a cylinder 33 fixed by a fixing tool 34 is connected to a front end of an arm 37 of a crank mechanism 36, rotational driving of a rotating body 38 by a motor causes the piston 35 to move back and forth, and thus a vibration can be imparted to the liquid for heating by periodically repeating suction and ejection of the liquid toward the balloon 3 via a connecting connector 28.

The suction and the ejection of the liquid for heating 14 are preferably repeated 1 to 5 times per second from a viewpoint of effectively generating eddy current in the interior of the balloon 3 and uniforming the surface temperature of the balloon in a short time.

A material for the pressure-resistant extension tube 8 is preferably a polyamide resin or polyvinyl chloride from a viewpoint of suppressing inner diameter fluctuation by pressure, the inner diameter is preferably 2 to 4 mm, and the length is preferably 0.5 to 2 m.

Also, an ablation catheter system with a balloon according to an embodiment of the present invention includes a catheter shaft, a balloon fixed to the catheter shaft, a lumen passing through the catheter shaft in a direction of a long axis to communicate with an interior of the balloon, a heating electrode arranged in the interior of the balloon, a heating device applying an electric energy to the heating electrode, and a vibration imparting device imparting a vibration to the liquid for heating by periodically repeating suction and ejection of the liquid for heating from the lumen, wherein the vibration is imparted to the liquid for heating so that a value derived by dividing a volume of the liquid for heating to be ejected from the lumen toward the balloon at a single time by an expansion volume of the balloon and multiplying the quotient by 100 becomes 2 to 9.

"The vibration imparting device" is preferably a device that can repeat the suction and the ejection of the liquid for heating 1 to 5 times per second from a viewpoint of effectively generating eddy current in the interior of the balloon 3 and uniforming the surface temperature of the balloon in a short time.

The device that can repeat the suction and the ejection of the liquid for heating 1 to 5 times per second is preferably a device having a pump selected from the group consisting of a roller pump, a diaphragm pump, a bellows pump, a vane pump, a centrifugal pump, and a pump constituted by combination of a piston and a cylinder from a viewpoint of the operation efficiency, configuration, and economics.

EXAMPLES

Hereinafter, specific examples of the stirring method and the ablation catheter system with a balloon according to embodiments of the present invention will be described with reference to the drawings. It is to be noted that "a length" represents a length in a longitudinal direction.

(Preparation of Ablation Catheter System with Balloon)

The balloon 3 made of polyurethane having an outer diameter of 25 mm and a film thickness of 40 μm was prepared by a blow molding method with use of Pellethane (manufactured by Dow Chemical Company). Also, the catheter shaft 2a made of polyurethane having an outer diameter of 3.3 mm, an inner diameter of 2.5 mm, and a length of 800 mm was prepared.

The lumen 4 was filled with 0.15 mL epoxy adhesive from a front end of the catheter shaft 2a, and a front portion of the lumen 4 was sealed. Also, the side hole 5 having a diameter of 2.5 mm was provided centering on a position 32 mm distanced in length from the front end of the catheter shaft 2a.

With a position 15 mm distanced in length from the front end of the catheter shaft 2a set as a starting point, a copper wire having an outer diameter of 0.4 mm plated with silver was wound in a proximal direction of the catheter shaft 2a to form the coiled heating electrode 9 having a length of 12 mm.

A copper wire having an outer diameter of 0.4 mm plated with silver as the heating electrode lead wire 11 was connected to the proximal end of the heating electrode 4 and was fixed by soldering. Meanwhile, the heating electrode lead wire 11 was coated with a Teflon (registered trademark) resin.

An extra fine thermocouple copper wire having an outer diameter of 0.1 mm as one temperature sensor lead wire 12 and an extra fine thermocouple constantan wire having an outer diameter of 0.1 mm as the other temperature sensor lead wire 12 were connected at the front ends and were fixed by soldering, and a T-shaped thermocouple obtained by the soldering was used as the temperature sensor 10. The temperature sensor 10 was fixed between the heating electrode 9 and the side hole 5 by adhesive. Meanwhile, the temperature sensor lead wire 12 was coated with a Teflon (registered trademark) resin.

The front portion of the balloon 3 was placed at a position 10 mm distanced in length from the front end of the catheter shaft 2a, and both ends of the balloon 3 were fixed on an outer circumference of the catheter shaft 2a by thermal welding.

A Y-shaped connector was attached to a proximal portion of the catheter shaft 2a, the heating electrode lead wire 11 and the temperature sensor lead wire 12 inserted into the lumen 4 were taken out from one opening of the connector, and the opening was sealed by adhesive.

The heating electrode lead wire 11 taken out from the opening of the Y-shaped connector was connected to the heating device 13, which is a radio-frequency generating device having a frequency of 1.8 MHz. Also, the temperature sensor lead wire 12 was connected to the temperature control unit in the heating device 13.

To the other opening of the Y-shaped connector was attached the three-way stopcock 7, to which the syringe and the pressure-resistant extension tube 8 that is a tube made of polyvinyl chloride having a length of 1 m, an inner diameter of 2 mm, and an outer diameter of 4 mm were respectively connected. To the other end of the pressure-resistant extension tube 8 was connected via the connecting connector 28 the syringe-type vibration imparting device 32 rotated 3 times per second, that is, the syringe-type vibration imparting device 32 repeating suction and ejection of the liquid for heating 3 times per second, and the ablation catheter system with a balloon was completed.

(Preparation for Use of Ablation Catheter System with Balloon)

A mixed solution at a volume ratio between a contrast medium (Hexabrix (registered trademark); manufactured by Guerbet KK) and saline of 1:1 was supplied from the syringe as the liquid for heating 14, air inside the interior of the balloon 3 and the lumen 4 were removed, and then the balloon 3 was expanded so that the maximum diameter thereof might be 25 mm.

Subsequently, the three-way stopcock 7 was switched to remove air inside the pressure-resistant extension tube 8, and the three-way stopcock 7 was further switched to make the syringe-type vibration imparting device 32 and the lumen 4 communicate with each other.

(Measurement of Volume of Liquid for Heating Ejected from Lumen)

FIG. 9 shows an experimental system to measure a volume of the liquid for heating to be sucked or ejected from the lumen by the vibration imparting device. The balloon 3 was removed from the ablation catheter with a balloon 1, and the lumen 4 and a scaled glass pipe 41 were made to communicate with each other via an attachment 40 fixed to correspond to a position of the side hole 5.

After air inside the lumen 4, the pressure-resistant extension tube 8, and the elastic tube 26 were removed, the liquid for heating 14 was supplied from the syringe attached to the three-way stopcock 7, and the liquid level in the glass pipe 41 was raised until the liquid level reached a 0 (mL) scale position.

Subsequently, after the three-way stopcock 7 was switched to make the pressure-resistant extension tube 8 and the lumen 4 communicate with each other, the vibration imparting device 6 was operated, and a scale value (mL) corresponding to the lower limit and a scale value (mL) corresponding to the upper limit of the liquid level moving up and down in the glass pipe 41 were read to regard a difference between the two values as a volume of the liquid for heating to be ejected from the lumen 4 toward the balloon 3 at a single time.

(Measurement of Surface Temperature of Balloon)

Figure 10:
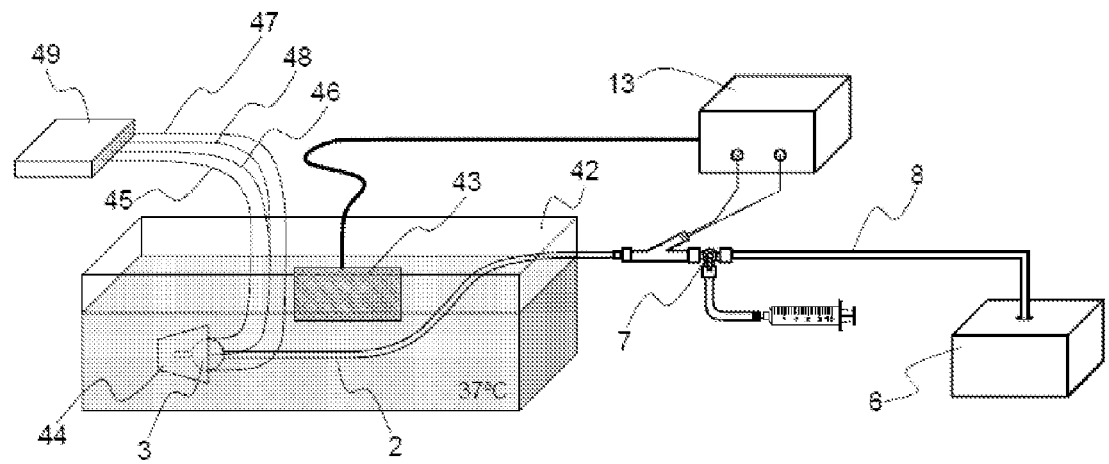
FIG. 10 shows an experimental system to measure a balloon surface temperature of the ablation catheter with a balloon.

FIG. 10 shows an experimental system to measure a balloon surface temperature of the ablation catheter with a balloon. A water tank 42 was filled with 35 L saline, and the temperature of the saline was kept at 37° C. A plate-like electrode 43 (model number 354; manufactured by Valley-Lab), serving as a counter electrode of the heating electrode 9, attached to an inner wall of the water tank 42 was connected to the heating device 13.

A pseudo myocardial tissue 44 made of polyacrylamide into a shape in which the balloon 3 expanded so that the maximum diameter thereof might be 25 mm would be fit was prepared in a transparent container and installed in the water tank 42.

Figure 11:
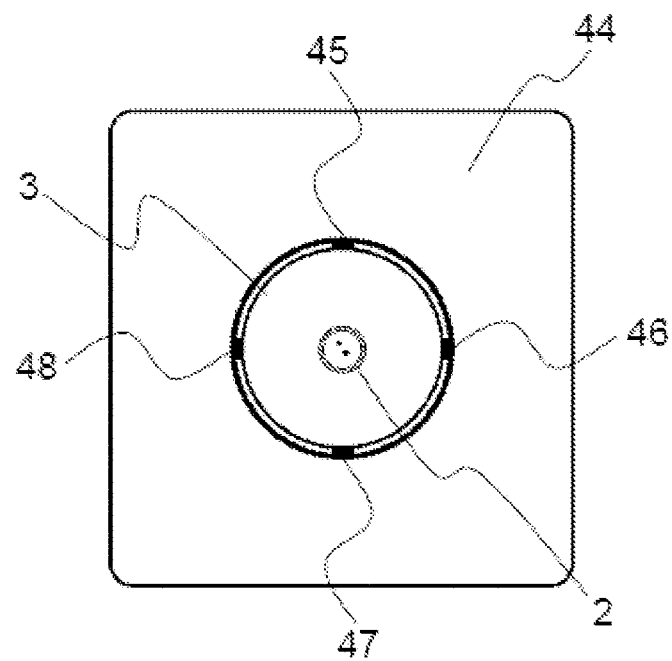
FIG. 11 shows positional relationship among a balloon, temperature sensors attached to the balloon, and a pseudo myocardial tissue in FIG. 10.

The balloon 3 was immersed into the saline in the water tank 42, was expanded so that the maximum diameter thereof might be 25 mm, and was fit into the pseudo myocardial tissue 44, and further temperature sensors 45 to 48, that is, temperature sensors A to D, were arranged at four locations in a circumferential direction of the balloon 3 at equal intervals and were respectively connected to a recording meter 49, as shown in FIG. 11.

The heating device 13 and the syringe-type vibration imparting device 32 were operated simultaneously, the balloon 3 was heated at a setting temperature of 70° C., and the temperatures of the balloon surfaces that the temperature sensors 45 to 48 contacted were respectively measured 120 seconds after the beginning of heating by the recording meter 49.

Example 1

Under a condition that a volume of the liquid for heating to be ejected from the lumen 4 toward the balloon 3 at a single time was adjusted to be 0.17 mL, the balloon surface temperatures were measured 120 seconds after the beginning of heating.

Example 2

Under a condition that a volume of the liquid for heating to be ejected from the lumen 4 toward the balloon 3 at a single time was adjusted to be 0.72 mL, the balloon surface temperatures were measured 120 seconds after the beginning of heating.

Comparative Example 1

Under a condition that a volume of the liquid for heating to be ejected from the lumen 4 toward the balloon 3 at a single time was adjusted to be 0.15 mL, the balloon surface temperatures were measured 120 seconds after the beginning of heating.

Comparative Example 2

Under a condition that a volume of the liquid for heating to be ejected from the lumen 4 toward the balloon 3 at a single time was adjusted to be 0.75 mL, the balloon surface temperatures were measured 120 seconds after the beginning of heating.

Table 1 shows a volume of the liquid for heating to be ejected from the lumen 4 toward the balloon 3 at a single time (hereinafter referred to as "ejected volume"), an expansion volume of the balloon 3 (hereinafter referred to as "balloon volume"), a value derived by dividing the volume of the liquid for heating to be ejected from the lumen 4 toward the balloon 3 at a single time by the expansion volume of the balloon 3 and multiplying the quotient by 100 (hereinafter referred to as "volume ratio"), and temperature measurement values of the temperature sensors A to D of each of EXAMPLES 1 and 2 and COMPARATIVE EXAMPLES 1 and 2. Table 1 also shows a difference between a maximum value and a minimum value of the temperature measurement values of the temperature sensors A to D (hereinafter referred to as "surface temperature difference").

TABLE 1

| Condition | Ejected volume (mL) | Balloon volume (mL) | Volume ratio | Temperature measurement value (° C.) | | | | Surface temperature difference |
|---|---|---|---|---|---|---|---|---|
| | | | | Sensor A | Sensor B | Sensor C | Sensor D | |
| Comparative example 1 | 0.15 | 8.18 | 1.83 | 58.0 | 54.8 | 51.0 | 55.1 | 7.0 |
| Example 1 | 0.17 | 8.18 | 2.08 | 56.3 | 55.8 | 55.1 | 55.8 | 1.2 |
| Example 2 | 0.72 | 8.18 | 8.80 | 57.1 | 56.8 | 56.6 | 57.0 | 0.5 |
| Comparative example 2 | 0.75 | 8.18 | 9.17 | 58.9 | 57.5 | 52.6 | 56.0 | 6.3 |

In EXAMPLE 1, in which the volume ratio was 2 or higher, the surface temperature difference of the balloon 3 was 2° C. or smaller, whereas in COMPARATIVE EXAMPLE 1, in which the volume ratio was 2 or lower, the surface temperature difference of the balloon 3 was as large as 7° C. or larger.

In the case where the volume ratio is 2 or lower, the ejected volume is too small, and stirring is not enough, which may cause a large surface temperature difference.

On the other hand, in EXAMPLE 2, in which the volume ratio was 9 or lower, the surface temperature difference of the balloon 3 was 1° C. or smaller, whereas in COMPARATIVE EXAMPLE 2, in which the volume ratio was 9 or higher, the surface temperature difference of the balloon 3 was as large as 6° C. or larger.

In the case where the volume ratio is 9 or higher, the ejected volume is too large, and the liquid for heating 14 sucked by the lumen 4 and cooled is ejected into the balloon 3 again in a large amount, which may cause a large surface temperature difference.

As is apparent from the result in Table 1, a value derived by dividing the volume of the liquid for heating to be ejected from the lumen 4 toward the balloon 3 at a single time by the expansion volume of the balloon 3 and multiplying the quotient by 100 is preferably in the range of 2 to 9 to eliminate a variation in the surface temperature of the balloon 3.

The present invention can be used as an ablation catheter system with a balloon for treatment of arrhythmias such as an atrial fibrillation, cancer cells, and the like.

DESCRIPTION OF REFERENCE SIGNS

1 . . . ablation catheter with a balloon, 2a, 2b, 2c . . . catheter shaft, 3 . . . balloon, 4, 4a, 4b . . . lumen, 5 . . . side hole, 6 . . . vibration imparting device, 7 . . . three-way stopcock, 8 . . . pressure-resistant extension tube, 9 . . . heating electrode, 10 . . . temperature sensor, 11 . . . heating electrode lead wire, 12 . . . temperature sensor lead wire, 13 . . . heating device, 14 . . . liquid for heating, 15 . . . ablation catheter system with a balloon, 20 . . . inner pipe, 21 . . . outer pipe, 22 . . . central lumen, 23 . . . guidewire, 24 . . . roller-pump-type vibration imparting device, 25 . . . rotating shaft, 26 . . . elastic tube, 27 . . . roller, 28 . . . connecting connector, 29 . . . sealing connector, 30 . . . guide surface, 31 . . . reservoir portion, 32 . . . syringe-type vibration imparting device, 33 . . . cylinder, 34 . . . fixing tool, 35 . . . piston, 36 . . . crank, 37 . . . arm, 38 . . . rotating body, 39 . . . adjusting groove, 40 . . . attachment, 41 . . . glass pipe, 42 . . . water tank, 43 . . . plate-like electrode, 44 . . . pseudo myocardial tissue, 45 . . . temperature sensor A, 46 . . . temperature sensor B, 47 . . . temperature sensor C, 48 . . . temperature sensor D, 49 . . . recording meter.

The invention claimed is:

1. A stirring method for stirring a liquid for heating by a vibration, the method comprising:
providing an ablation catheter system with a balloon, the ablation catheter system comprising a catheter shaft, the balloon fixed to the catheter shaft, the balloon having a film thickness of 20 µm to 100 µm, a lumen passing through the catheter shaft in a direction of a longitudinal axis to communicate with an interior of the balloon, a heating electrode arranged in the interior of the balloon, a heating device, and a vibration imparting device;
applying with the heating device an electric energy to the heating electrode;
imparting with the vibration imparting device a vibration to a liquid for heating by periodically repeating suction and ejection of the liquid for heating from the lumen; and
wherein the vibration is imparted to the liquid for heating so that a value derived by dividing a volume of the liquid for heating to be ejected from the lumen toward the balloon at a single time by an expansion volume of the balloon and multiplying the quotient by 100 becomes 2 to 9 and the imparting with the vibration imparting device repeats the suction and the ejection of the liquid for heating 1 to 5 times per second.

2. An ablation catheter system, comprising:
a catheter shaft;
a balloon fixed to the catheter shaft, the balloon having a film thickness of 20 µm to 100 µm;
a lumen passing through the catheter shaft in a direction of a longitudinal axis to communicate with an interior of the balloon;
a heating electrode arranged in the interior of the balloon;
a heating device applying an electric energy to the heating electrode; and
a vibration imparting device imparting a vibration to a liquid for heating by periodically repeating suction and ejection of the liquid for heating from the lumen,
wherein the vibration is imparted to the liquid for heating so that a value derived by dividing a volume of the liquid for heating to be ejected from the lumen toward the balloon at a single time by an expansion volume of the balloon and multiplying the quotient by 100 becomes 2 to 9 and the imparting with the vibration imparting device repeats the suction and the ejection of the liquid for heating 1 to 5 times per second.

3. The ablation catheter system according to claim 2, wherein the vibration imparting device includes a pump selected from the group consisting of a roller pump, a diaphragm pump, a bellows pump, a vane pump, a centrifugal pump, and a pump constituted by combination of a piston and a cylinder.

* * * * *